United States Patent
Gisel et al.

(10) Patent No.: US 6,549,808 B1
(45) Date of Patent: Apr. 15, 2003

(54) DEVICES AND METHODS FOR THE TRANSCUTANEOUS DELIVERY OF IONS AND THE ELECTRICAL STIMULATION OF TISSUE AND CELLS AT TARGETED AREAS IN THE EYE

(76) Inventors: Heinz R. Gisel, 310 Nautilus St., La Jolla, CA (US) 92037; Ryuichi Hayama, 2-8-1 Harigaya, Urawa-shi, Saitama 338-0805 (JP); Tatsuo Tsunoda, 2-2-1 Midori-cho, Koganei-shi, Tokyo 184-0003 (JP)

( * ) Notice: Subject to any disclaimer, the term of this patent is extended or adjusted under 35 U.S.C. 154(b) by 182 days.

(21) Appl. No.: 09/692,843

(22) Filed: Oct. 19, 2000

(51) Int. Cl.[7] .............................. A61N 1/20; A61N 1/36
(52) U.S. Cl. ......................................... 607/53; 607/139
(58) Field of Search ........................... 607/53, 139, 141

(56) References Cited

U.S. PATENT DOCUMENTS

| | | | | |
|---|---|---|---|---|
| 4,052,572 A | * | 10/1977 | Schafer | 607/56 |
| 4,331,163 A | * | 5/1982 | Nomura | 607/141 |
| 6,083,251 A | * | 7/2000 | Shindo | 607/53 |

FOREIGN PATENT DOCUMENTS

| JP | 7-289649 | * 11/1995 | ............ A61N/1/32 |
|---|---|---|---|

OTHER PUBLICATIONS

Abstract, Treatment of Seasonal Affective Disorder with a High–Output Negative Ion Generator; Michael Terman, Ph.D. and Jiuan Su Terman, Ph.D. Journal of Alternative and Complementary Medicine, 1:87–92, 1995.

Air Ion Effects on Human Performance; A review of literature commissioned by Ecstatic Ltd., 51 Royden Court, Mayfield Rd, Walton on Thames, Surrey KT12 5HZ.

* cited by examiner

*Primary Examiner*—Andrew M. Dolinar
(74) *Attorney, Agent, or Firm*—Nydegger & Associates

(57) ABSTRACT

A device for electrically exciting tissue in the uveal and periuveal areas of the eye includes a frame similar to an eyeglass frame in shape and construction. Two flat, disk-shaped electrodes are attached to the frame. When the frame is placed on the head of the patient, the electrodes are positioned adjacent the orbits of the patient's eyes. A voltage source and electronic circuitry is provided to establish a voltage differential between the electrodes thereby allowing electrical currents to flow from one electrode to the other, stimulating the tissue and other cells in the uveal and periuveal areas of the eyes. Alternatively, the patient's body can be isolated from ground and the voltage source used to place a negative charge on each electrode to thereby create beneficial negative ions in the uveal and periuveal areas of each eye.

9 Claims, 2 Drawing Sheets

DEVICES AND METHODS FOR THE TRANSCUTANEOUS DELIVERY OF IONS AND THE ELECTRICAL STIMULATION OF TISSUE AND CELLS AT TARGETED AREAS IN THE EYE

FIELD OF THE INVENTION

The present invention pertains generally to devices and methods useful for electrical excitation of tissue. More particularly, the present invention pertains to devices and methods useful for the transcutaneous delivery of ions and the electrical stimulation of tissue and cells at targeted areas of the body. The present invention is particularly, but not exclusively, useful for generating negative ions and producing electrical currents in the uveal and periuveal areas of the eyes.

BACKGROUND OF THE INVENTION

Electrical stimulation of tissue in the major muscle groups such as the arms and legs by externally supplied electrical signals has been shown to relax and strengthen muscle tissue. When used in this way, the externally supplied electrical signals are similar to the electrical signals supplied by the nervous system to contract and relax the muscles. By the exercise of targeted muscles, damage associated with strain, fatigue and overuse can be repaired. Electrical stimulation of tissue is often used as part of a prescribed physical therapy program for this purpose. Further, electrical stimulation of tissue is known to dilate nearby blood vessels, increasing circulation and effectively increasing metabolism and the amount of beneficial oxygen available for targeted tissues such as muscle tissue and nerve tissue.

Additionally, devices have been disclosed which generate ions (negatively or positively charged particles) and release the ions into the air for contact with nearby individuals. Contacting the body with ions is known to produce certain therapeutic results. Specifically, ion generators that produce negative ions have been used with some success to reduce the effects of asthma, allergies and hayfever. Some research also indicates that an environment rich in negative ions may alter brain wave activity thereby reducing depression and anxiety, and increasing alertness. Unfortunately, airborne ions are often ineffective because the exposure level to airborne ions is generally low. Additionally, airborne ions tend to be neutralized quickly after contact with the body, rendering the airborne ions ineffective. Further, the rate at which the airborne ions are neutralized is increased if the body is in contact with an electrical ground. Finally, it is difficult to reach specific tissues and cells in targeted areas of the body with airborne ions. Nevertheless, it may be desirable to target specific areas of the body for ion therapy, electrical stimulation, or both. For purposes of the present invention, both ion therapy and electrical stimulation are considered types of electrical excitation. Examples of areas of the body that may be desirable to target include areas where an increase in circulation may be beneficial. For example, the penis may be targeted in individuals suffering from erectile dysfunction (ED). Another desirable target area may include the sinuses in individuals suffering from allergies, hayfever or asthma. For individuals with ophthalmic deficiencies, the eye and areas surrounding the eye may be targeted.

The muscle tissue, nerve tissue and other cells found in and around the eye are critical for proper eyesight and function. For example, the ciliary muscles of the eye are relied upon to focus on objects by changing the shape of the lens of the eye. Additionally, muscles in and around the eye allow for eyeball movement thereby enabling a person to see in different directions. Smaller muscles within the eye allow the iris to open and close in response to changes in external lighting conditions. Like all muscles, the muscles of the eye are subject to fatigue and strain due to overuse, as well as the effects of aging. If the performance of the eye muscles such as the ciliary muscles become impaired, normal eye function can be adversely affected. For example, it is known that when the performance of the ciliary muscles is impaired, the time required to focus in response to a sudden change in lighting conditions increases substantially. Further, the performance of the retinal cells and the tissues in the optic nerve can affect visual acuity.

In light of the above, it is an object of the present invention to provide devices and methods suitable for the purposes of electrically exciting tissue and other cells in targeted areas of the body. It is another object of the present invention to provide devices capable of generating both negative ions and currents for electrical stimulation in the uveal and periuveal areas of the eye to restore optimal eye function by increasing blood flow and metabolism. It is yet another object of the present invention to provide devices and methods capable of generating pulsed electrical currents and/or time-varying electrical currents in the uveal and periuveal areas of the eye to thereby allow treatments tailored to a particular vision deficiency. It is yet another object of the present invention to provide devices and methods for electrically exciting muscle tissue, nerve tissue and other cells to increase blood flow and available oxygen at target areas within the body. Yet another object of the present invention is to provide devices and methods for electrical excitation of tissue and other cells at target areas in the body which are easy to use, relatively simple to manufacture, and comparatively cost effective.

SUMMARY OF THE PREFERRED EMBODIMENTS

The present invention is directed to devices and methods for electrically exciting tissue and other cells at target locations within the body. In one embodiment of the present invention, a device is disclosed for use in electrically exciting tissue and other cells in the uveal and periuveal areas of an eye. In this embodiment, the device includes a frame that is very similar to an eyeglass frame in shape and construction. The frame is formed with a bridge section and a pair of supports. Each support has a first end which is affixed to and extends from the bridge section, and a second end which rests upon the ear of the patient. When the frame is positioned on the head of the patient, the bridge section rests against the nose of the patient and each support rests upon one of the patient's ears. Preferably, the frame is constructed of a flexible plastic material which allows the frame to be slightly expanded during positioning on the patient's head to thereby afford a snug, stable fit when positioned properly on the patient's head.

A pair of conductive electrodes is attached to the frame. Preferably, each electrode is disk-shaped and has a circular contact surface. The contact surface can be flat or have a slight curvature and is preferably approximately thirty millimeters (30 mm) in diameter and gold plated. A first electrode is attached to one of the supports and a second electrode is attached to the other support. Each electrode is attached to a support between the end of the support that is affixed to the bridge section and the end of the support that rests on the ear of the patient. Specifically, the electrodes are located on the supports to position the first electrode adjacent the orbit of one eye, while positioning the second electrode adjacent the orbit of the other eye. When the frame is properly positioned on the patient's head, the contact surface of the first electrode is held against the orbit of one of the patient's eyes, and similarly, the contact surface of the second electrode is held against the orbit of the patient's other eye. It is to be appreciated that other frame configurations can be used to hold a pair of electrodes against a different target area such as the sinuses.

A power unit is provided that includes a voltage source for applying a voltage to the electrodes to thereby electrically excite the tissue and other cells in the uveal and periuveal areas of the eyes. Electronic circuitry is provided for allowing the voltage to be applied to the electrodes in two distinct modes (described in detail below). The power unit includes a housing to contain the voltage source and electronic circuitry. The first electrode is electrically connected to the power unit by a first wire, and the second electrode is electrically connected to the power unit by a second wire.

When the power unit is used in the first mode (ion-therapy mode), the patient's body is isolated from ground (i.e. earth-ground), and the voltage source is used to simultaneously place an equal charge on each electrode. Preferably, a negative charge is placed on each electrode to thereby create beneficial negative ions in the uveal and periuveal areas of each eye. In this first mode, a direct current (DC) voltage source having approximately 200 volts is provided. The positive lead from the voltage source establishes the reference potential of the power unit. The negative lead from the voltage source is then electrically connected to both the first electrode and the second electrode. Consequently, in the first mode, each electrode is maintained at the same potential and no electrical current flows from one electrode to the other. Instead, due to whatever potential differences there may be between the electrodes and the body, current will flow from the electrodes and into the body to create negative ions. Preferably, the electrodes, when positioned on the patient, are charged (i.e. connected to the voltage source) for a period between approximately three minutes and approximately fifteen minutes.

In the second mode (electrical stimulation mode), the voltage source can be used to establish a voltage differential between the first electrode and the second electrode thereby allowing electrical currents to flow from the first electrode, through the uveal and periuveal areas of the eyes, to the second electrode. A voltage differential of up to approximately 5 volts can be applied to the electrodes to stimulate the tissue and other cells in the uveal and periuveal areas of the eyes. Electronic circuitry is provided in the power unit to allow the magnitude of the voltage to be varied over time and/or to allow the voltage to be pulsed. For the present invention, the voltage can be periodically reversed thereby allowing electric current to initially flow from the first electrode to the second electrode and subsequently flow from the second electrode to the first electrode. For certain treatments, the voltage can be configured as a pulse package having a sequence of pulses. The sequence of pulses can be made to increase in a substantially linear manner from a zero voltage to an absolute voltage. The increasing pulses may be followed by a sequence of pulses decreasing from the absolute voltage to zero voltage. For some treatments, the voltage can be configured as a pulse package having a first sequence of pulses and a second sequence of pulses. For the present invention, the polarity of the voltage used for the first sequence of pulses can be reversed for the second sequence of pulses.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
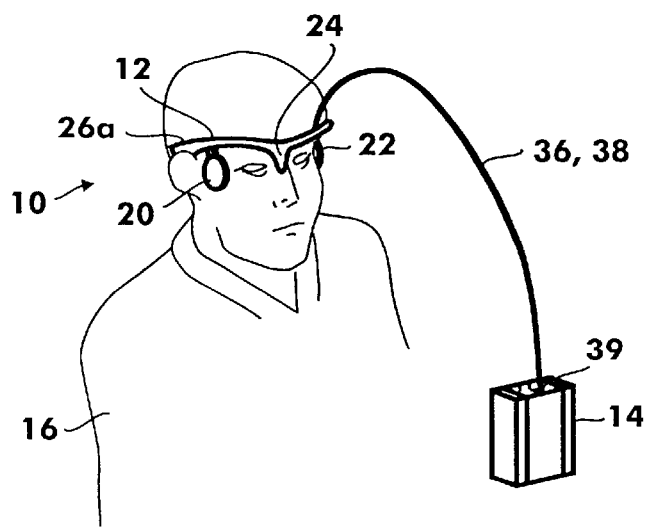
FIG. 1 is a perspective view of a patient being treated with a device in accordance with the present invention.
Figure 2:
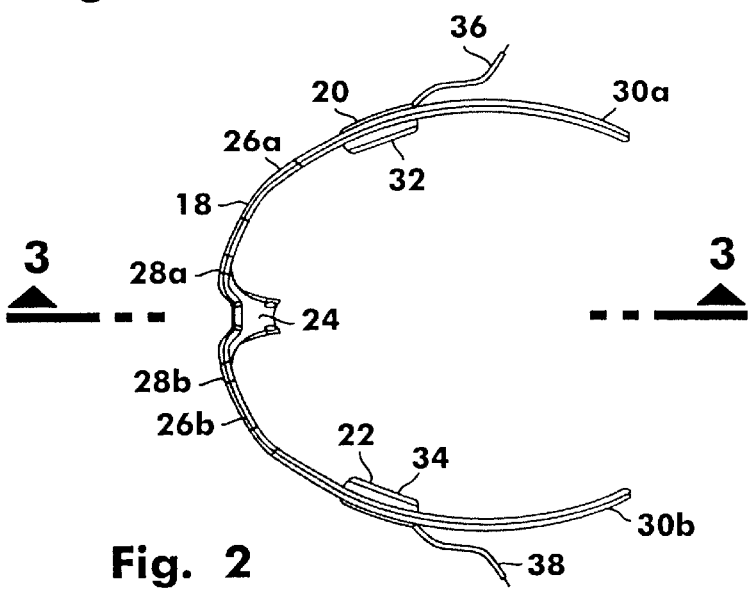
FIG. 2 is a plan view of a headset in accordance with the present invention showing the frame and electrodes.
Figure 3:
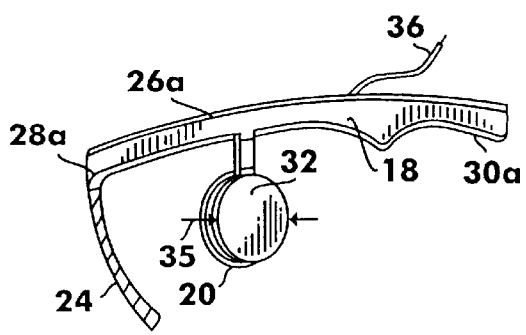
FIG. 3 is a cross-sectional view of the headset as shown along line 3—3 in FIG. 2.

Referring to FIG. 1, a device for electrically exciting the tissue and other cells at the target area of a body in accordance with the present invention is shown and, generally designated 10. For the device 10 shown, the target area is the uveal and periuveal areas of the eyes. As shown in FIG. 1, the device 10 includes a headset 12 and a power unit 14. FIG. 1 shows the headset 12 positioned on the head of a patient 16. The construction of the headset 12 can best be seen with reference to FIGS. 2 and 3. As shown in FIGS. 2 and 3, the headset includes a frame 18 and a pair of electrodes 20, 22. The frame 18 is formed with a bridge section 24 and a pair of supports 26a,b. Each support 26a,b has an end 28a,b that is attached to the bridge section 24. Further, each support 26a,b extends from the bridge section 24 and terminates in an end 30a,b. Preferably, the frame 18 is constructed from a flexible plastic material.

As further shown in FIGS. 2 and 3, electrode 20 is attached to support 26a, between the end 28a of the support 26a and the end 30a of the support 26a. Similarly, electrode 22 is attached to support 26b between the end 28b of the support 26b and the end 30b of the support 26b. Preferably, as shown, each electrode 20, 22 is disk-shaped, made of a conductive material and has a flat (or slightly curved), circular contact surface 32, 34 that is gold plated. In the preferred embodiment of the present invention, each contact surface 32, 34 has a diameter 35 of approximately thirty millimeters (30 mm).

Referring back to FIG. 1, when the headset 12 is properly positioned on the head of the patient 16, the bridge section 24 of the frame 18 rests against the nose of the patient 16 and each support 26 rests upon a different ear of the patient 16. Further, with combined reference to FIGS. 1, 2 and 3, it can be seen that when the headset 12 is properly positioned on the head of the patient 16, the contact surface 32 of the electrode 20 is positioned adjacent one of the orbits of the eye of the patient 16. Similarly, the contact surface 34 of the electrode 22 is positioned adjacent one of the orbits of the eye of the patient 16.

Referring now to FIGS. 1 and 2, it can be seen that a wire 36 is provided to electrically connect the electrode 20 to the power unit 14. Similarly, a wire 38 is provided to electrically connect the electrode 22 to the power unit 14. Further, a mode switch 39 is provided to allow the power unit 14 to be reconfigured between a first configuration for ion therapy and a second configuration for electrical stimulation.

Figure 4A:
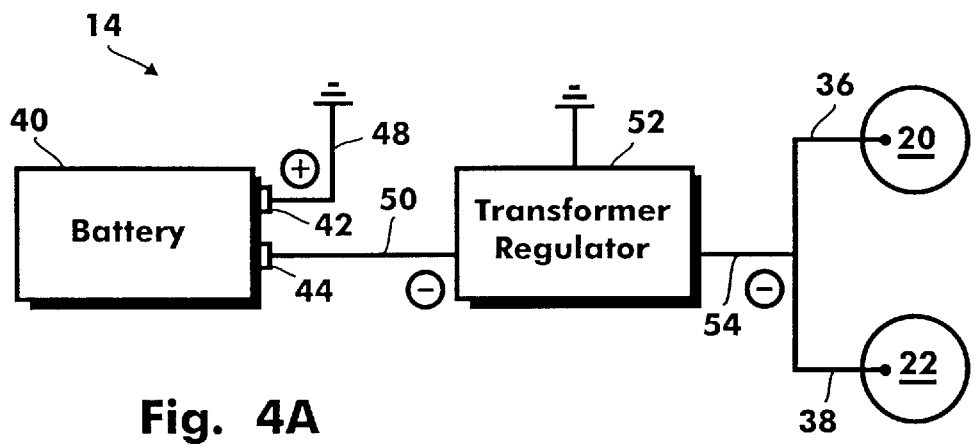
FIG. 4A is a functional block diagram of are presentative power unit configured for ion therapy.

FIG. 4A shows a functional block diagram for a representative power unit 14 in accordance with the present invention configured in the first configuration for ion therapy. When the power unit 14 is configured for ion therapy, the body of the patient 16 must be isolated from electrical ground (i.e. earth ground). In ion therapy mode, the power unit 14 is used to place a negative charge on each electrode 20, 22. As shown in FIG. 4A, the power unit 14 preferably includes a DC battery 40 having a positive terminal 42 and a negative terminal 44. Also shown, in the first mode, the positive lead 48 is connected to the positive terminal 42 of the battery 40, and establishes the reference potential of the power unit 14. The negative terminal 44 of the battery 40 is electrically connected to negative lead 50, which in turn is electrically connected to an optional transformer/regulator 52. Lead 54 electrically connects the optional transformer/regulator 52 to both wires 36, 38 which in turn electrically connect lead 54 to the electrodes 20, 22. Consequently, in the first mode, there is essentially no potential difference between the two electrodes 20, 22 and no current flows from one electrode 20, 22 to the other electrode 20, 22. Instead, due to whatever potential differences there may be between the electrodes 20, 22 and the body of the patient 16, electrons will flow from the electrodes 20, 22 and into the body of the patient 16 to create negative ions. The optional transformer/regulator 52 provides an increased voltage differential (voltage differential between the negative lead 50 and the positive lead 48) than is presented by the battery 40. Preferably, a voltage differential between the negative lead 50 and the positive lead 48 of approximately 200 volts is established, thereby producing a negative charge on each electrode 20, 22. Preferably, the negative charge is placed on the electrodes 20, 22 for a period of between approximately three minutes and approximately fifteen minutes.

Figure 4B:
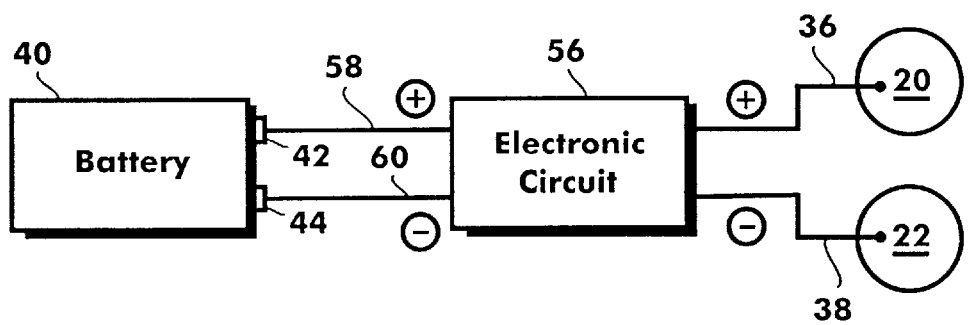
FIG. 4B is a functional block diagram of a representative power unit configured for electrical stimulation.

FIG. 4B shows a functional block diagram for a representative power unit 14 in accordance with the present invention configured in the second configuration for electrical stimulation. As discussed above, the mode switch 39 (shown in FIG. 1) can be used to reconfigure the power unit 14 between the first configuration for ion therapy and the second configuration for electrical stimulation.

When configured in the second mode, the power unit 14 can be used to establish a voltage differential, $V_{20/22}$, between the electrode 20 and the electrode 22, thereby allowing electrical currents to flow from one electrode 20, 22 through the uveal and periuveal areas of the eyes, to the other electrode 20, 22. A voltage differential, $V_{20/22}$, of up to approximately 5 volts can be applied to the electrodes 20, 22 to stimulate the muscle tissue in the orbital and periuveal areas of the eyes.

As shown in FIG. 4B, electronic circuit 56 is provided in the power unit 14 to allow the magnitude of the voltage, $V_{20/22}$, to be varied over time and/or to allow the voltage, $V_{20/22}$, to be pulsed. For the present invention, the electronic circuit 56 can also allow the voltage, $V_{20/22}$, to be periodically reversed thereby allowing an electrical current to initially flow from electrode 20 to electrode 22 and subsequently flow from electrode 22 to electrode 20. For the present invention, the electronic circuit 56 can be any circuit or set of circuits known in the pertinent art capable of varying the voltage, $V_{20/22}$, with time, creating voltage pulses, or reversing the polarity of the voltage, $V_{20/22}$.

As shown in FIG. 4B, in the second mode, the terminals 42, 44 of the battery 40 are electrically connected to positive lead 58 and negative lead 60, which in turn, are electrically connected to the electronic circuit 56. Also shown in FIG. 4B, the electronic circuit 56 is electrically connected to wires 36, 38 which in turn, electrically connect the electronic circuit 56 to the electrodes 20, 22.

Figure 5:
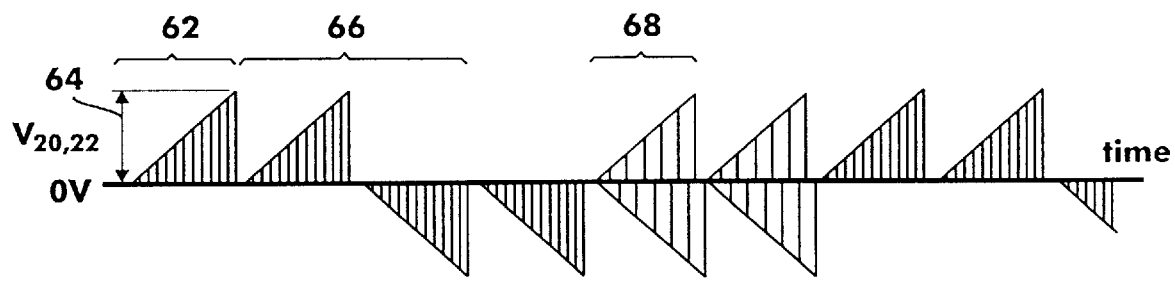
FIG. 5 is a graph showing the voltage difference between the two electrodes, $V_{20/22}$, plotted as a function of time for an exemplary treatment plan.

FIG. 5 shows an exemplary treatment plan for electrical stimulation in accordance with the present invention. It is to be appreciated that the treatment plan shown in FIG. 5 is only exemplary, and that any type of waveform may be used including pulsed signals, non-pulsed signals, constant voltage signals, and alternating voltage signals. As shown in FIG. 5, a sequence of voltage pulses (represented by vertical lines) of varying magnitude and polarity can be used. For convenience, a discrete number or sequence of pulses can be grouped together and referred to as a pulse package. For example, FIG. 5 shows a pulse package 62 that includes a plurality of positive pulses of voltage, $V_{20/22}$. As shown in FIG. 5, a pulse package such as pulse package 62 can be configured with a sequence of pulses that increase in a substantially linear manner from a zero voltage to an absolute voltage 64. The increasing pulses may be followed by a sequence of pulses of opposite sign, also increasing in magnitude from zero voltage to an absolute voltage 64, such as the pulse package 66, shown in FIG. 5. Further, FIG. 5 shows a pulse package 68 wherein the magnitude of the voltage, $V_{20/22}$ increases in a substantially linear manner from a zero voltage to an absolute voltage 64, but the polarity of each pulse alternates from positive to negative.

While the particular devices and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A device for electrical excitation of tissue in a patient which comprises:

a frame formed with a means for holding said frame in a substantially stationary position on the patient;

at least one electrode mounted on said frame, said electrode being adjacent the tissue when said frame is in said position; and a voltage source having a first lead and a second lead, said first lead connected to said electrode for passing an electrical current through the tissue and wherein said voltage source produces a direct current (DC) voltage of approximately 200 volts between said electrode and said second lead.

2. A device as recited in claim 1 comprising a first said electrode and a second said electrode, with said first electrode adjacent one orbit of the patient and with said second electrode adjacent another orbit of the patient when said frame is in said position, and wherein each electrode is in electrical contact with said first lead.

3. A device as recited in claim 1 wherein said electrode is shaped as a disk.

4. A device as recited in claim 3 wherein said disk is approximately thirty millimeters (30 mm) in diameter.

5. A device as recited in claim 1 wherein selected portions of said disk are gold plated.

6. A method for generating negative ions in the uveal and periuveal areas of an eye of a patient comprising the steps of:

proviпонуding a frame having at least one electrode mounted on said frame;

positioning said frame on the head of the patient to hold said electrode adjacent an orbit; and applying a voltage to said electrode to generate negative ions in the uveal and periuveal areas of an eye.

7. A method as recited in claim 6 wherein said voltage is applied to said electrode for approximately 15 minutes.

8. A method as recited in claim 6 wherein said voltage is approximately negative 200 volts.

9. A method for electrical stimulation of cells in the uveal and periuveal areas of the eyes of a patient comprising the steps of:

providing a frame having a first electrode mounted on said frame and a second electrode mounted on said frame;

positioning said frame on the head of the patient to hold said first electrode adjacent one orbit of the patient and said second electrode adjacent the other orbit of the patient; and applying a voltage to said electrodes to pass an electrical current from the first electrode, through the uveal and periuveal areas of the eyes, to the second electrode, wherein said voltage is a pulse package having a first sequence of pulses of a first voltage sign, said first sequence of pulses increasing in a substantially linear manner from a zero voltage to an absolute voltage followed by a second sequence of pulses of a second voltage sign, said second sequence of pulses increasing in a substantially linear manner from a zero voltage to an absolute voltage and wherein said second voltage sign is opposite said first voltage sign.

* * * * *

UNITED STATES PATENT AND TRADEMARK OFFICE
CERTIFICATE OF CORRECTION

PATENT NO.      : 6,549,808 B1                                                   Page 1 of 1
DATED           : April 15, 2003
INVENTOR(S)     : Heinz R. Gisel, Ryuichi Hayama and Tatsuo Tsunoda It is certified that error appears in the above-identified patent and that said Letters Patent is hereby corrected as shown below:

<u>Column 4,</u>
Line 15, delete "are presentative" insert -- a representative --

Signed and Sealed this

Seventeenth Day of June, 2003

JAMES E. ROGAN
*Director of the United States Patent and Trademark Office*